(12) United States Patent
Smirnov et al.

(10) Patent No.: US 12,138,033 B2
(45) Date of Patent: Nov. 12, 2024

(54) SYSTEM AND METHOD FOR POLYP DETECTION THROUGH CAPSULE DYNAMICS

(71) Applicant: CHECK-CAP LTD., Isfiya (IL)

(72) Inventors: Michael Smirnov, Haifa (IL); Hadas Shahar, Ramat Yishay (IL); Shlomo Lewkowicz, Tivon (IL); Alex Ovadia, Haifa (IL); Yoav Kimchy, Haifa (IL); Boaz Shpigelman, Natanya (IL)

(73) Assignee: CHECK-CAP LTD., Isfiya (IL)

( * ) Notice: Subject to any disclaimer, the term of this patent is extended or adjusted under 35 U.S.C. 154(b) by 812 days.

(21) Appl. No.: 17/261,580

(22) PCT Filed: Feb. 6, 2019

(86) PCT No.: PCT/IL2019/050147
§ 371 (c)(1),
(2) Date: Jan. 20, 2021

(87) PCT Pub. No.: WO2020/021524
PCT Pub. Date: Jan. 30, 2020

(65) Prior Publication Data
US 2021/0267475 A1    Sep. 2, 2021

Related U.S. Application Data

(60) Provisional application No. 62/702,922, filed on Jul. 25, 2018.

(51) Int. Cl.
*A61B 5/07* (2006.01)
*A61B 5/00* (2006.01)
*A61B 5/06* (2006.01)

(52) U.S. Cl.
CPC .............. *A61B 5/073* (2013.01); *A61B 5/067* (2013.01); *A61B 5/4255* (2013.01); *A61B 5/7264* (2013.01); *A61B 5/7275* (2013.01)

(58) Field of Classification Search
CPC ....... A61B 5/073; A61B 5/067; A61B 5/4255; A61B 5/7264; A61B 5/7275
(Continued)

(56) References Cited

U.S. PATENT DOCUMENTS 7,200,253 B2    4/2007  Glukhovsky et al.
8,068,897 B1 *  11/2011 Gazdzinski .......... A61B 5/0071
                                                    600/128
(Continued)

FOREIGN PATENT DOCUMENTS

JP    2003-126045 A1    5/2003
JP    2006-297109 A2    11/2006
(Continued)

OTHER PUBLICATIONS

Gluck et.al., "A novel prepless X-ray imaging capsule for colon cancer screening", Gut Online First, published on Dec. 1, 2015 as 10.1136/gutjnl-2015-310893.

*Primary Examiner* — William D Titcomb
(74) *Attorney, Agent, or Firm* — SOROKER AGMON NORDMAN RIBA

(57) ABSTRACT

A system for polyp detection through capsule dynamics, including a capsule configured to be swallowed by a patient, a recorder configured to be worn by the patient and to receive transmission of information from the capsule, wherein the system is configured to determine position or motion information of the capsule from the information received from the capsule, analyze the position or motion information and determine a probability score representing the likelihood of the existence of polyps in the gastrointestinal tract of the patient; and wherein the system notifies the patient of further actions to be performed in response to the determined probability score.

16 Claims, 7 Drawing Sheets

(58) Field of Classification Search
USPC .......................................................... 382/128
See application file for complete search history.

(56) References Cited

U.S. PATENT DOCUMENTS

| | | | | |
|---|---|---|---|---|
| 8,682,142 B1* | 3/2014 | Boskovitz | ............ | G11B 27/034 |
| | | | | 386/282 |
| 9,042,952 B2* | 5/2015 | Lynn | ...................... | A61B 5/087 |
| | | | | 600/324 |
| 9,392,961 B2 | 7/2016 | Kimchy et al. | | |
| 9,844,354 B2 | 12/2017 | Kimchy et al. | | |
| 11,147,468 B2* | 10/2021 | Kimchy | ............... | A61B 5/6833 |
| 2003/0139661 A1* | 7/2003 | Kimchy | ................. | A61B 5/073 |
| | | | | 600/407 |
| 2004/0054278 A1* | 3/2004 | Kimchy | ................. | A61B 6/425 |
| | | | | 600/407 |
| 2004/0204630 A1* | 10/2004 | Gilad | ........................ | A61B 5/06 |
| | | | | 600/117 |
| 2005/0281446 A1* | 12/2005 | Glukhovsky | .......... | A61B 1/042 |
| | | | | 382/128 |
| 2007/0066875 A1* | 3/2007 | Horn | ....................... | A61B 1/041 |
| | | | | 600/300 |
| 2007/0076930 A1* | 4/2007 | Zinaty | .................... | A61B 1/041 |
| | | | | 424/9.1 |
| 2008/0146871 A1* | 6/2008 | Arneson | ............. | A61B 5/6861 |
| | | | | 600/101 |
| 2009/0023993 A1* | 1/2009 | Davidson | ............. | A61B 1/0005 |
| | | | | 382/128 |
| 2010/0183210 A1* | 7/2010 | Van Uitert | ............ | G06T 7/0012 |
| | | | | 382/131 |
| 2010/0303200 A1* | 12/2010 | Kimchy | ................ | A61B 6/4057 |
| | | | | 378/44 |
| 2012/0071710 A1* | 3/2012 | Gazdzinski | ............... | A61B 8/12 |
| | | | | 600/101 |
| 2013/0197360 A1* | 8/2013 | Baum | ...................... | A61B 1/31 |
| | | | | 600/431 |
| 2014/0031642 A1 | 1/2014 | Kimchy et al. | | |
| 2014/0039287 A1* | 2/2014 | Adler | ................... | A61B 5/0084 |
| | | | | 600/371 |
| 2015/0223727 A1* | 8/2015 | Kimchy | ................. | A61B 5/065 |
| | | | | 600/302 |
| 2016/0066813 A1 | 3/2016 | Kimchy et al. | | |
| 2018/0153385 A1* | 6/2018 | Arneson | ................ | A61B 1/041 |
| 2018/0214004 A1* | 8/2018 | Kamon | .............. | A61B 5/14552 |

FOREIGN PATENT DOCUMENTS

| | | |
|---|---|---|
| JP | 2008-506419 A | 3/2008 |
| JP | 2015-533537 T2 | 11/2015 |
| JP | 2016-063868 A1 | 8/2017 |
| WO | 2008/096358 A2 | 8/2008 |

\* cited by examiner

SYSTEM AND METHOD FOR POLYP DETECTION THROUGH CAPSULE DYNAMICS

RELATED APPLICATIONS

The present application claims priority from U.S. Provisional application No. 62/702,922 filed on Jul. 25, 2018 the disclosure of which is incorporated herein by reference.

TECHNICAL FIELD

The present disclosure relates generally to a system and method utilizing capsule dynamics in the gastrointestinal tract or colon of a patient to evaluate the probability of the presence of polyps, lesions or cancerous growths in the colon and or rectum.

BACKGROUND

One method for examining the gastrointestinal tract for the existence of polyps and other clinically relevant features that may provide an indication regarding the potential of cancer is performed by swallowing an imaging capsule that will travel through the gastrointestinal (GI) tract and view the patient's situation internally. In a typical case the trip can take between 24-72 hours, after which the imaging capsule exits in the patient's feces.

U.S. Pat. No. 9,844,354, the disclosure of which is incorporated herein by reference describes use of an X-ray based imaging capsule that is capable of performing Colorectal Cancer Screening (CRC) to detect polyps, lesions and cancerous growths in the colon. The capsule detects changes in morphology of the colon by measuring the distances from the capsule to the colon wall and reconstructing 2D and 3D maps of the colon walls. A system including the capsule can also use a tracking system to monitor the position of the capsule such as described in US patent application publication 2014/0031642 and US patent application publication 2016/0066813, the disclosures of which are incorporated herein by reference.

SUMMARY

An aspect of an embodiment of the disclosure relates to a system and method for detecting polyps, lesions or cancerous growths in a gastrointestinal tract of a patient based on dynamics of a capsule swallowed by the patient. The system includes a recorder that it worn by the patient and receives transmissions from the capsule to determine position or motion information of the capsule. A probability score is determined based on the position or motion information transmitted by the capsule. The probability score may be determined based on a motion pattern of the capsule through the gastrointestinal tract or based on the time required for the capsule to traverse the gastrointestinal tract or specific organs of the gastrointestinal tract.

The probability score determination is based on the discovery that the motion of the capsule in a patient with polyps tends to differ from the motion of the capsule in a user without polyps. Likewise the time required to traverse the gastrointestinal tract of a patient tends to be longer for patients with polyps relative to patients without polyps. In an exemplary embodiment of the disclosure, a statistical model or a neural network or other machine learning algorithm can be trained to determine the probability score of the existence of polyps based on the capsule motion. Optionally, when the travel time of the capsule exceeds a limit it is a clear indication of the existence of polyps.

In an exemplary embodiment of the disclosure, the use of a capsule without imaging capability has the benefits of not requiring any preparations such as using laxatives as required for optically based imaging capsules. Likewise the patient does not need to drink a contrast agent and is not subject to radiation as with an X-ray based imaging capsule. By monitoring the motion of the capsule and analyzing the motion with a trained analysis program many patients can be diagnosed without risk and at a reduced cost. In some cases the results are less definitive and the aid of images may help to provide a more accurate determination. Optionally, the patient can use a first capsule without imaging capability and if necessary use a second capsule with imaging capability, for example if the first capsule was not decisive.

There is thus provided according to an exemplary embodiment of the disclosure, a system for polyp detection through capsule dynamics, comprising:
A capsule configured to be swallowed by a patient;
A recorder configured to be worn by the patient and to receive transmission of information from the capsule;
Wherein the system is configured to determine position or motion information of the capsule from the information received from the capsule, analyze the position or motion information and determine a probability score representing the likelihood of the existence of polyps in the gastrointestinal tract of the patient; and
Wherein the system is configured to notify the patient of further actions to be performed in response to the determined probability score.

In an exemplary embodiment of the disclosure, the capsule includes imaging capability and the information provided by the capsule enables reconstruction of images of the gastrointestinal tract of the patient. Optionally, if the probability score is higher than a high threshold value the images are ignored and the patient is notified to perform a colonoscopy. In an exemplary embodiment of the disclosure, if the probability score is lower than a low threshold value the images are ignored and the Patient is notified that further testing is not required. Optionally, if the probability score is lower than a high threshold value and higher than a low threshold value the images are analyzed to determine if to perform a colonoscopy. In an exemplary embodiment of the disclosure, the system includes motion monitoring capability of the capsule within the gastro intestinal tract of the patient that enables determining a motion pattern of the capsule in the gastrointestinal tract of the patient and the system determines the probability score of the existence or absence of polyps based on the motion pattern. Optionally, the motion pattern is analyzed by a statistical model or a neural network classifier to determine the probability score. In an exemplary embodiment of the disclosure, the approximate location of the polyp or which organ has a polyp is determined based on the motion pattern. Optionally, the information from the capsule also enables determining a time interval for traversing the gastrointestinal tract or specific organs and the probability score is based also on the time interval. In an exemplary embodiment of the disclosure, the information from the capsule enables determining a time interval for traversing the gastrointestinal tract or specific organs and the probability score is based on the time interval.

There is further provided according to an exemplary embodiment of the disclosure, a method of detecting polyps in a gastrointestinal tract of a patient with a system including a capsule and a recorder based on capsule dynamics, comprising:

Swallowing the capsule;

Wearing the recorder, which is capable of receiving transmissions of information from the capsule;

Determining position or motion information of the capsule from the information received from the capsule;

Analyzing the position or motion information to determine a probability score representing the likelihood of the existence of polyps in the gastrointestinal tract of the patient; and Notifying the patient of further actions to be performed responsive to the determined probability score.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
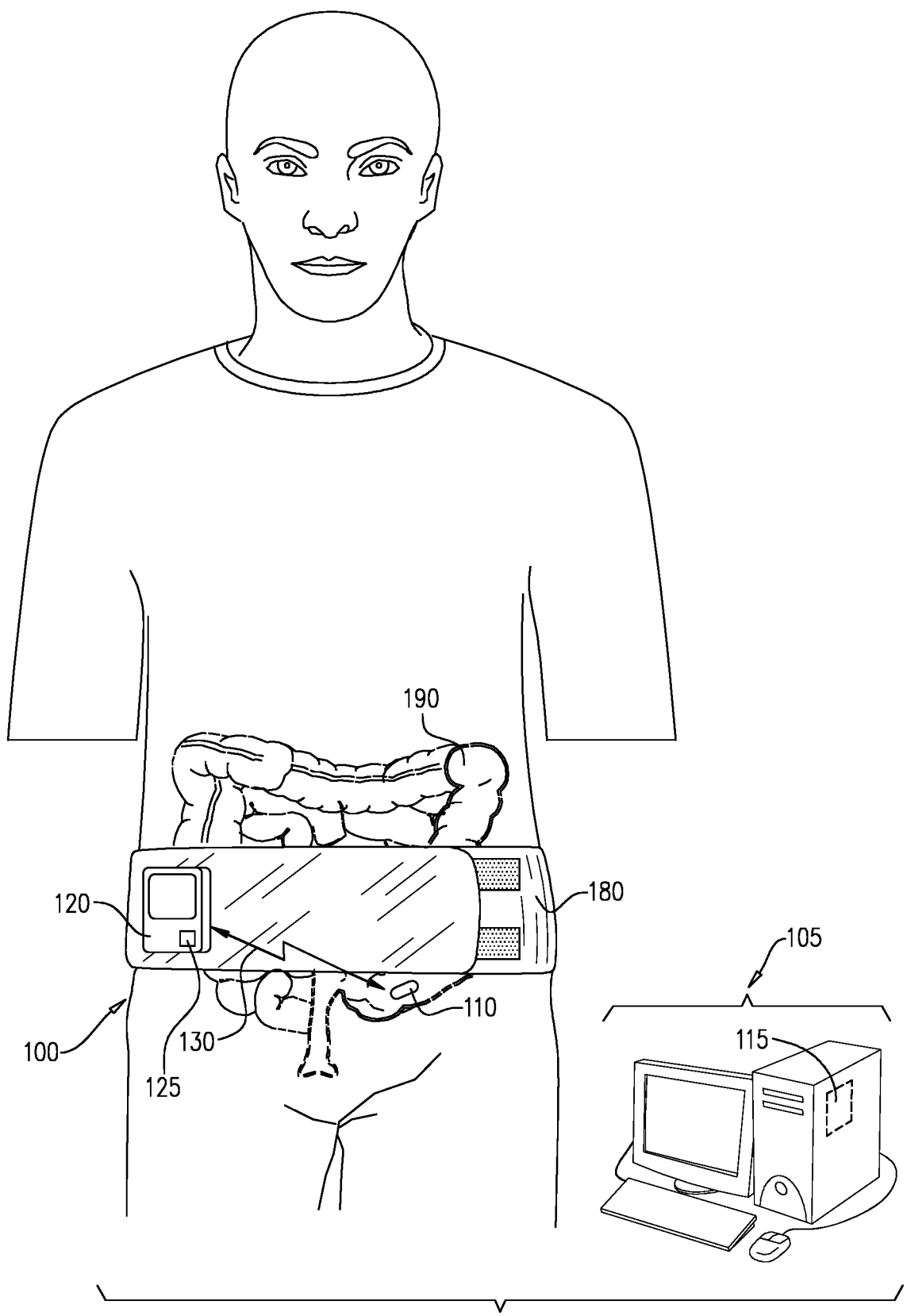
FIG. 1 is a schematic illustration of a system for estimating the position of a capsule inside the body of a patient, according to an exemplary embodiment of the disclosure.

FIG. 1 is a schematic illustration of a system 100 for determining if a user has polyps or cancerous growths. System 100 includes a capsule 110 and an external recorder 120. Recorder 120 communicates with capsule 110 and optionally monitors the motion of capsule 110 inside the body of a patient. In an exemplary embodiment of the disclosure the patient swallows capsule 110. The capsule 110 enters the Gastro Intestinal tract of the patient and transmits 130 position information to the recorder 120. Optionally, the information includes details regarding the position of the capsule 110 within the patient or signals from which recorder 120 can determine the position of the capsule 110.

The position information may include identifying transitions from organ to organ, for example transition from the small intestine to the cecum, from the cecum to the colon 190, from the colon 190 to the rectum and/or exiting from the rectum. Additionally, the position information may include three dimensional coordinates of the capsule and/or orientation information. Optionally, recorder 120 may use the information to monitor and record the position, velocity and/or acceleration of the capsule 110 within the patient. In some embodiments of the disclosure, capsule 110 may include an imaging system that records images or details for constructing images from within the patient and transmit 130 the image information to recorder 120. Optionally, the image information enables construction of a three dimensional image of the patient's colon and/or other organs.

In an exemplary embodiment of the disclosure, the information recorded by recorder 120 is used to determine the position and motion of the capsule within the body of the patient. Optionally, recorder 120 may process the information independently or may store the information on a non-transitory memory card 125 so that it may be provided to a computer 105 for analysis. Alternatively, the information may be transmitted wirelessly or over a communication line to the computer 105 in real-time or after completing the journey of the capsule 110 through the patient's body.

In an exemplary embodiment of the disclosure, recorder 120 and/or computer 105 incorporate a program 115 to analyze the capsule motion information and determines a probability score indicating if the patient has a polyp or other abnormalities (the term polyp will be used in this disclosure to refer to polyps, cancerous growths, lesions or other abnormalities). The analysis determines the probability score based on the motion pattern (see e.g. FIGS. 8 and 9) and/or travel time of capsule 110 through the different organs of the gastrointestinal tract. In some embodiments of the disclosure, a high probability score above a high threshold value indicates that the patient has polyps with a high probability. In contrast a low probability value, for example below a low threshold value may indicate that it is very unlikely that the patient has polyps.

In an exemplary embodiment of the disclosure, if the travel time of the capsule through the patient's body is greater than 60 or 70 hours the score will be above the high threshold value. Optionally, if the travel time is low, then the score will be lower than the high threshold value but might be higher than the low threshold value. In such a case the computer 105 may request to evaluate acquired images to provide a determination if the patient needs further testing. In some embodiments of the disclosure, the probability score may be based on the travel time through specific organs (e.g. the stomach, small intestine, colon and rectum). Alternatively or additionally, the probability score is based on the motion pattern of capsule 110 through specific organs (e.g. the colon) and not just on the travel time. Optionally, computer 105 may notify recorder 120 of the probability score to notify the patient, for example by providing a message on a display of the recorder 120.

In an exemplary embodiment of the disclosure, recorder 120 is coupled to a strap or belt 180 to keep it fixated to the patient's body in proximity to the small intestine and colon 190 as they are examined by capsule 110. The recorder 120 may be positioned on the front of the patient, the back of the patient or in any selected position. Optionally, the position is selected empirically to provide optimal readings from transmissions 130 provided by capsule 110. In an exemplary embodiment of the disclosure, recorder 120 analyzes transmissions from capsule 110 to determine the spatial position of capsule 110 relative to recorder 120.

Figure 2:
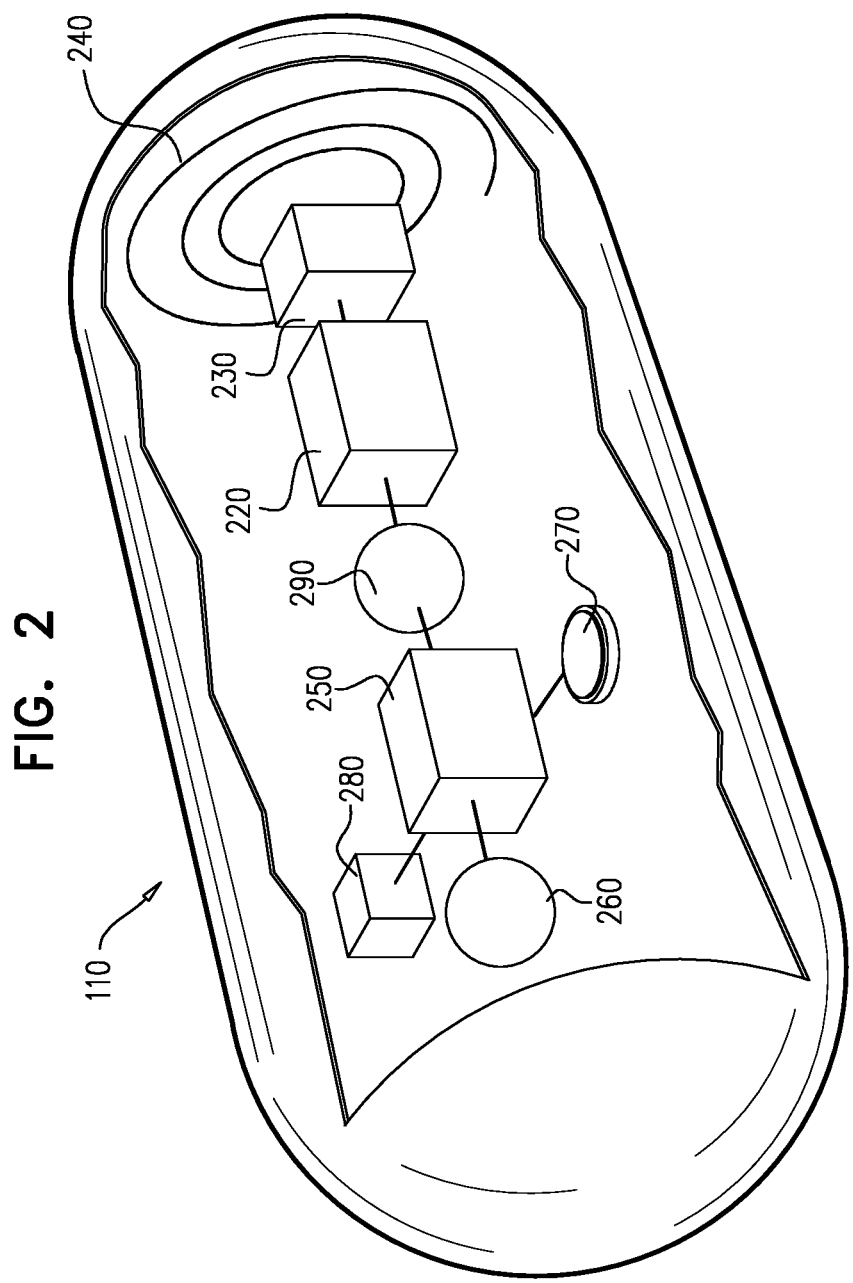
FIG. 2 is a schematic illustration of a capsule, according to an exemplary embodiment of the disclosure.

FIG. 2 is a schematic illustration of capsule 110, according to an exemplary embodiment of the disclosure. Optionally, capsule 110 includes a coil 240 for transmitting a low frequency electromagnetic wave, for example at 1-50 Khz to enable recorder 120 to determine the position of the capsule 110. Alternatively, the transmission of an electromagnetic signal may be at approximately 7-14 MHz and the signal can then be used for both localization and data transmission, for example using a communication system on a chip such as NxH2180 manufactured by NXP Semiconductors from Eindhoven, The Netherlands. With this implementation, the communication information will be extracted from the coil with a good signal to noise ratio (SNR).

Optionally, the transmissions are received by recorder 120 and their amplitudes are analyzed to determine the location of capsule 110. In some embodiments of the disclosure, the windings of coil 240 reside in a single plane. Alternatively, coil 240 may include windings in two or three orthogonal planes (a coil with windings in two orthogonal planes is referred to as a 2D coil and a coil with windings in three orthogonal planes is referred to as a 3D coil). Optionally, a 3D coil transmits in three orthogonal directions and uses more energy than a coil transmitting in a single plane. Accordingly, in some embodiments of the disclosure, capsule 110 may be designed to use a single plane coil 240 to conserve power (e.g. provided by a battery 270), and to enable a relatively large coil that improves power efficiency. In contrast recorder 120 that is located outside the patient's body may use a 3D coil since its power source can be larger and can easily be replaced if necessary.

In an exemplary embodiment of the disclosure, capsule 110 includes a magnetometer 230 that functions as a 3D geomagnetic sensor (e.g. MAG3110 manufactured by Freescale Semiconductors Ltd from Austin Tex.). Alternatively or additionally, capsule 110 includes an accelerometer 220 that functions to sense changes in the direction of capsule 110, for example in colon 190. MMA7260QT manufactured by Freescale Semiconductors LTD is an example of a small sized accelerometer that can be incorporated into capsule 110. In some embodiments of the disclosure, a combined magnetometer and accelerometer can be used, for example FXOS8700CQ manufactured by Freescale Semiconductors LTD.

In some embodiments of the disclosure, capsule 110 may include an imaging system 270 that collects information for constructing images from within the patient. Optionally, imaging system 290 may include a light source, a camera and lenses, or a radiation source and a detector to scan the patient with radiation.

In an exemplary embodiment of the disclosure, capsule 110 includes a controller 250 and a transceiver 260 to control the functionality of capsule 110 and communicate with recorder 120. The controller 250 may include a processor and/or memory to receive and execute software instructions. Optionally, controller 250 can receive instructions via transceiver 260, for example to start scanning and to stop scanning. Additionally, controller 250 can transmit images recorded by capsule 110 and information regarding the spatial position of the capsule 110, for example the readings of the magnetometer 230 and/or the accelerometer 220. Optionally, the information can notify recorder 120 regarding the orientation of imaging capsule 110 and coil 240 relative to the magnetic field and gravitational field of the earth.

In some embodiments of the disclosure, capsule 110 may include additional sensors, such as a pressure sensor 280, which can help to identify transitions between different organs.

Figure 3:
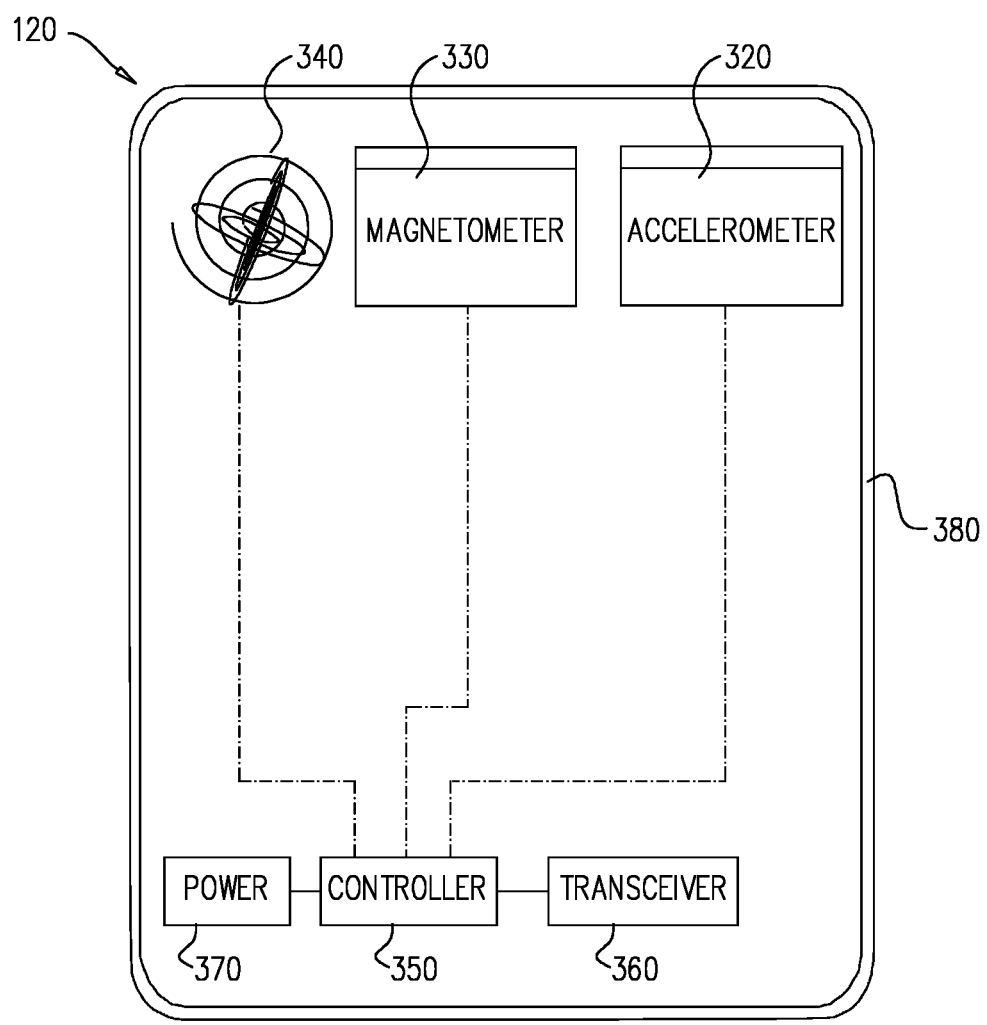
FIG. 3 is a schematic illustration of a recorder, according to an exemplary embodiment of the disclosure.

FIG. 3 is a schematic illustration of recorder 120, according to an exemplary embodiment of the disclosure. Optionally, recorder 120 may include a controller 350, a transceiver 360, a magnetometer 330, an accelerometer 320, a power source 370 and one or more reception coils 340. Optionally, the one or more reception coils 340 may be single plane coils or have windings in two or three orthogonal planes (a 2D coil or a 3D coil). In an exemplary embodiment of the disclosure, one or more reception coils 340 of recorder 120 interact with coil 240 of capsule 110 by receiving the low frequency transmissions transmitted from capsule 110. Optionally, analysis of the amplitude of the transmissions from capsule 110 by a combination of reception coils 340 can be used to determine the direction and distance from recorder 120 so that the spatial location of the capsule 110 can be calculated and the distance between the recorder 120 and the capsule 110 can be determined.

In an exemplary embodiment of the disclosure, readings from magnetometer 230 and/or accelerometer 220 are transmitted from capsule 110 to recorder 120. Optionally, recorder 120 compares the readings with the readings of magnetometer 330 and/or accelerometer 320 to determine the angular direction of capsule 110 and coil 240 relative to the direction of recorder 120 and the one or more reception coils 340. In an exemplary embodiment of the disclosure, the readings of magnetometer 230 and/or accelerometer 220 are transmitted with a timestamp from capsule 110 to synchronize comparison of the readings of magnetometer 230 and/or accelerometer 220 with the readings of magnetometer 330 and/or accelerometer 320. Optionally, the amplitudes measured by the one or more reception coils 340 from the transmissions of coil 240 with the angular direction determined from the readings of magnetometer 230 and/or accelerometer 220 are used to determine the spatial location of capsule 110 relative to recorder 120.

In an exemplary embodiment of the disclosure, electromagnetic disturbances to the transmissions of coil 240 can be identified, for example by controller 350 of recorder 120 since the spatial angles of capsule 110 are acquired by magnetometer 330 and/or accelerometer 320. Optionally, in the case of an external magnetic or metallic disturbance the electromagnetic field will be disturbed differently then the constant earth magnetic field and/or the gravitational field. Therefore a sudden change in the amplitude of the transmissions from coil 240 without a matching change in the spatial orientation of capsule 110 as recorded by the magnetometer 330 and/or accelerometer 320 can provide an indication regarding an electromagnetic disturbance that can be disregarded. In some embodiments of the disclosure, the coil amplitude will be processed only when movement of the capsule 110 is detected.

In an exemplary embodiment of the disclosure, the distance to the capsule 110 is calculated using two or more reception coils 340 at recorder 120 without information from accelerometer 220 and/or magnetometer 230. In an exemplary embodiment of the disclosure, the two or more reception coils may have windings in a single plane or may have windings in two or three orthogonal planes. In some embodiments of the disclosure at least one of the reception coils 340 is a 3D coil. Optionally, the position is determined by testing all possible directions for the capsule 110 and selecting the direction for which the two or more reception coils 340 reach agreement for the calculated position of the capsule 110. Optionally, the agreement takes into account the position difference between the two or more reception coils 340 in recorder 120. In an exemplary embodiment of the disclosure, one of the reception coils 340 may serve as a transmitter and receiver to provide transmissions to the other reception coils 340 so that the relative distance and angles between the reception coils 340 in the recorder 120 can be measured before calculating the distance to coil 240. Alternatively, a separate transmitting reference coil is used and distance is calculated relative to that reference.

In some embodiments of the disclosure, coil 240 in capsule 110 is a 3D coil that transmits simultaneously in three different frequencies, or alternatively transmits with a single frequency but the windings of each orthogonal plane transmit sequentially so that the receiver can distinguish between the three transmissions. Optionally, a single planar reception coil 340 may be used to receive the transmissions and calculate the distance from recorder 120 and capsule 110 at that moment.

In an exemplary embodiment of the disclosure, recorder 120 includes an encasement 380 (FIG. 3). Optionally, encasement 380 is coated with a high permeability material that shields the elements of recorder 120 from the influence of magnetic fields outside the body, for example such as MuMetal manufactured by The MuShield Company from Londonderry, New Hampshire, USA. In an exemplary embodiment of the disclosure, the side facing the patient's body is not coated so that it can receive transmissions from capsule 110 from inside the patient's body. Optionally, the effect of the shielding if any is calibrated by recorder 120 so that it is shielded from external electromagnetic interference.

In an exemplary embodiment of the disclosure, the conclusions of this application are based on data from clinical trials on patients with and without polyps, and motility data of the capsules. In an exemplary experiment presented in table 1 below a correlation is shown between colon movements and the presence of polyps in the colon and or the rectum.

TABLE 1

|  | Total | polyp | no polyp | NA | Avg age tested | Avg age Healthy | Avg age Polyp |
| --- | --- | --- | --- | --- | --- | --- | --- |
| Male | 108 | 63 | 41 | 4 | 58 | 53 | 61 |
| Female | 58 | 24 | 30 | 4 | 57 | 54 | 61 |

| | GI Avg time +/− std deviation | |
| --- | --- | --- |
| | Male | Female |
| Healthy | 38 +/− 16 | 56 +/− 25 |
| Polyp | 58 +/− 37 | 54 +/− 40 |

Table 1 shows the results from 166 Patients out of which 87 patients had polyps in their colon and/or rectum. As can be appreciated from this table, a clear correlation can be seen for male patients between GI transit time and the presence of polyps. The table separates between men and women since the data are somewhat different between these two genders and the data in this study was biased with male patients being ⅔ of the tested population.

Figure 4:
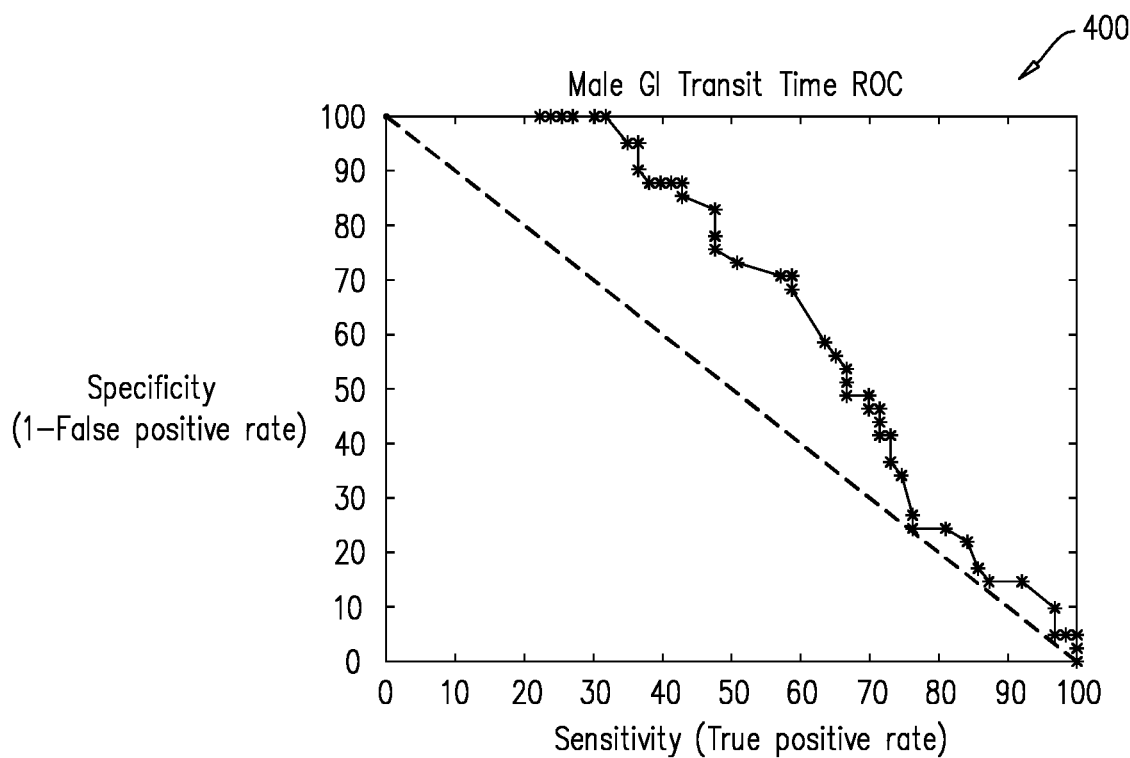
FIG. 4 is a chart of a Receiving Operating Characteristic (ROC) for men taking GI transit time as the detection parameter for polyps, according to an exemplary embodiment of the disclosure.

FIG. 4 shows a Receiving Operating Characteristic Chart (ROC Chart) 400 for men, taking GI transit time as the detection parameter for polyps. Sensitivity (True Positive Rate) and specificity (1-False Positive Rate) for the detection of the presence of polyps in these patients can be seen for the GI transit time parameter which is extracted from the motility data from capsule 110 and recorder 120 as described above.

Statistical analysis of the data shows that for men, 19 patients with a GI transit time parameter above 70 hours had polyps, estimating 100% sensitivity for the presence of polyps in the colon and or rectum and 100% specificity. The margin of error for this parameter predicting the presence of a polyp is smaller than 5%.

Analyzing time in cecum+time in colon (total colon time) for men and women, it was shown that above 72 hours, 22 patients had polyps and 2 had no polyps out of 166 patients that participated in the study with a total of 87 patients with polyps. This corresponds to sensitivity for this motility parameter of 25% and a specificity of 89%.

In an exemplary embodiment of the disclosure, capsule 110 is continuously tracked by recorder 120 and motility of capsule 110 is used to predict the presence of polyps. That is, if the motility parameter such as GI transit time is above a preselected threshold value, then the Patient will be considered to have a high probability of a polyp and system 100 will provide a recommendation to send the patient to perform a colonoscopy for further diagnosis regardless of the results of images or other measurements that may be provided by capsule 110. Optionally, determination of slow motility of a capsule 110 in a patient, may be used to predict the presence of polyps as a complimentary indicator in addition to detecting polyps by an imaging capsule as described in applications mentioned in the background. Alternatively, a capsule 110 without imaging capability may be used thus not exposing the patient to radiation and not requiring any preparations at all, even drinking a contrast agent is not required.

In an exemplary embodiment of the disclosure, for patients with normal motility, a capsule with x-ray imaging capability enables good coverage and scanning of the colon and uses the x-ray imaging for the detection of polyps or other abnormalities in the colon. For patients with slow motility, that may have less than optimal colon coverage (e.g. due to running out of power after being so long inside the patient) and hence non optimal imaging of the colon, the motility parameter such as GI transit time can give an indication on the presence of a polyp in the colon and or rectum. For this scenario, if the motility parameter such as GI transit time is above a set threshold, then the patient will be considered to have high probability of a polyp and will be sent to perform a colonoscopy for further diagnosis regardless of the imaging results. Optionally, if the motility parameter such as GI transit time is below the set threshold, than the presence of a polyp will be determined by the imaging results.

In an exemplary embodiment of the disclosure, other capsule motility parameters such as time in Cecum, Colon transit time and total colon time can be used to characterize and differentiate between patients with polyps and patients without polyps.

Figure 5:
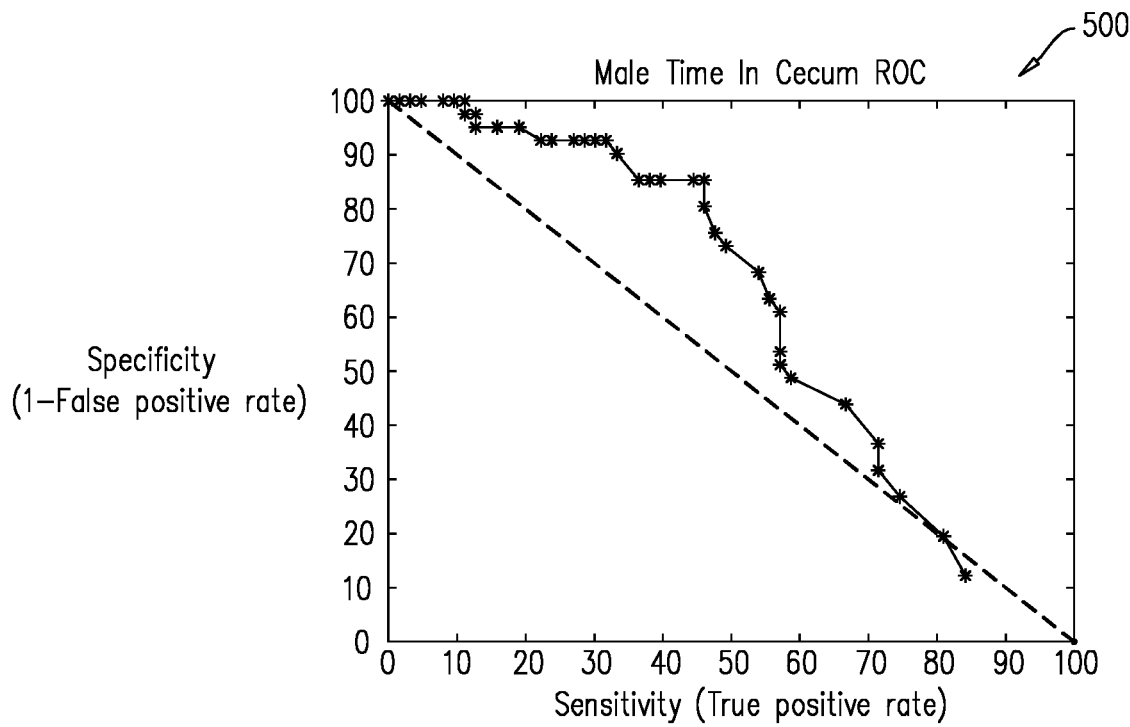
FIG. 5 is a chart of a Receiving Operating Characteristic (ROC) for men, taking Cecum transit time as the detection parameter for polyps, according to an exemplary embodiment of the disclosure.

FIG. 5 shows a Receiving Operating Characteristic Chart (ROC Chart) 500 for men, taking Cecum transit time as the detection parameter for polyps.

Figure 6:
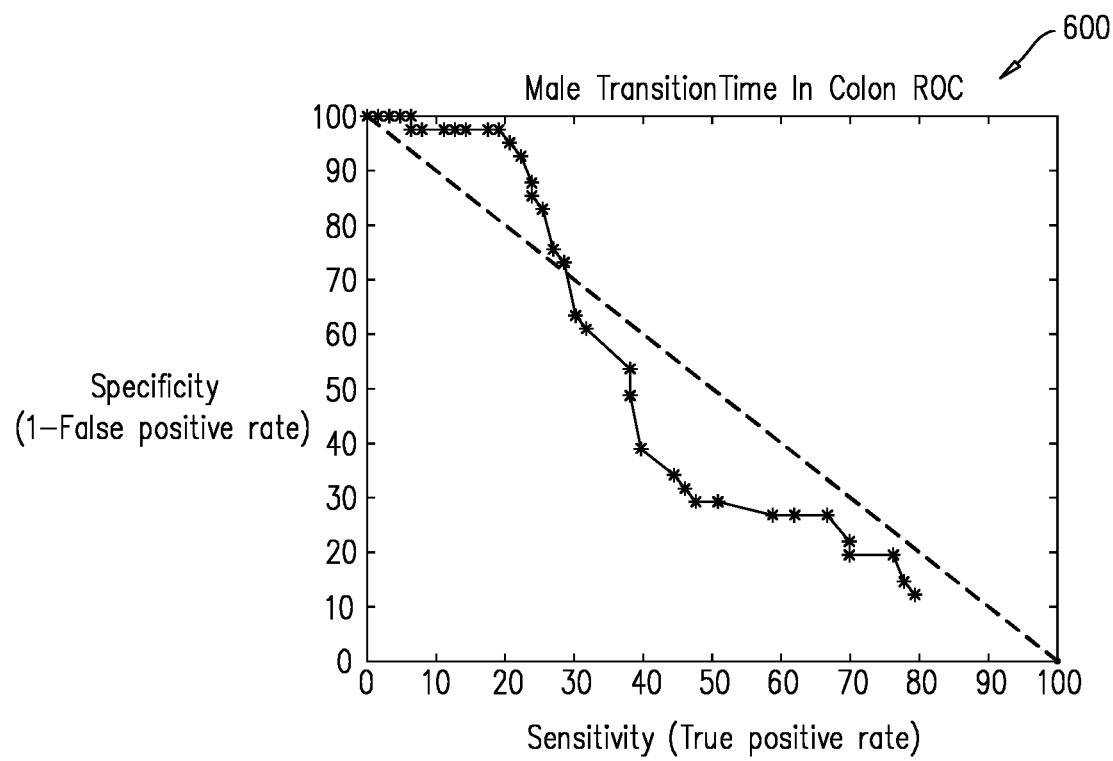
FIG. 6 is a chart of a Receiving Operating Characteristic (ROC) for men, taking Colon transit time as the detection parameter for polyps, according to an exemplary embodiment of the disclosure.

FIG. 6 shows a Receiving Operating Characteristic Chart (ROC Chart) 600 for men, taking Colon transit time as the detection parameter for polyps.

Figure 7:
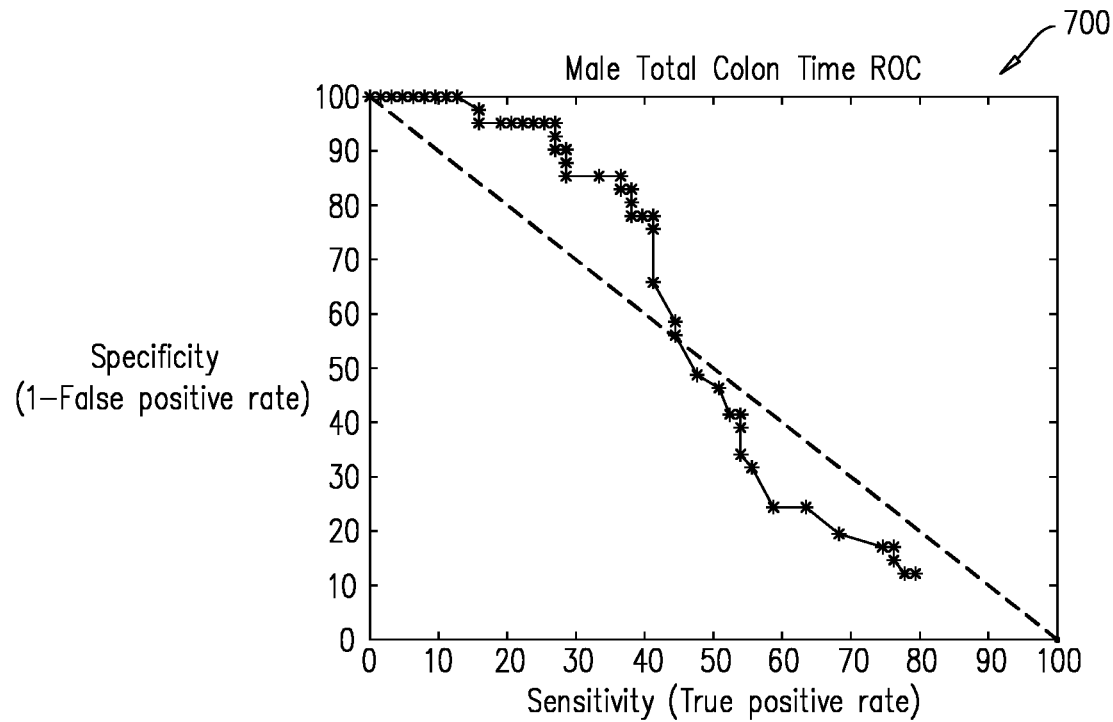
FIG. 7 is a chart of a Receiving Operating Characteristic (ROC Chart) for men, taking total colon (Cecum+Colon) transit time as the detection parameter for polyps, according to an exemplary embodiment of the disclosure.

FIG. 7 shows a Receiving Operating Characteristic Chart (ROC Chart) 700 for men, taking total colon (Cecum+ Colon) transit time as the detection parameter for polyps.

In an exemplary embodiment of the disclosure, the dynamics of capsule 110 are analyzed for capsule movements and capsule velocities.

Figure 8:
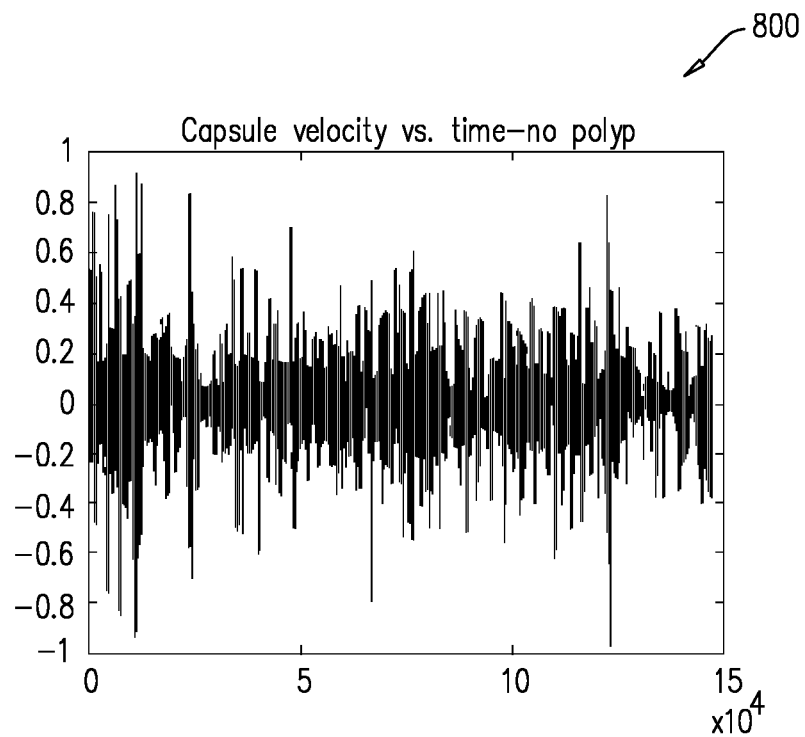
FIG. 8 is a graph of capsule velocities as a function of time when no polyp was detected, according to an exemplary embodiment of the disclosure.
Figure 9:
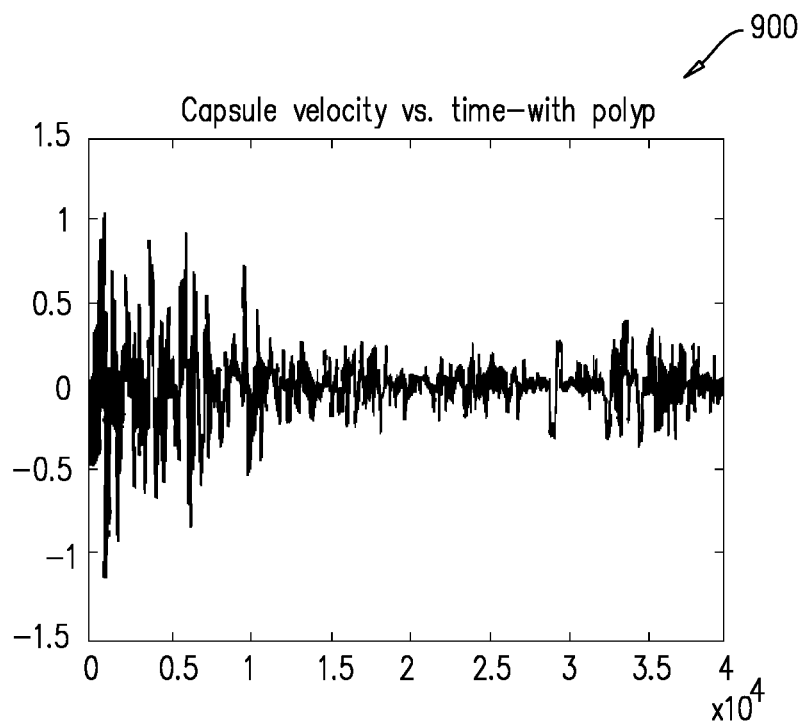
FIG. 9 is a graph of capsule velocities as a function of time when a polyp was detected, according to an exemplary embodiment of the disclosure.

FIG. 8 is a graph 800 of capsule velocities as a function of time when no polyp was detected and FIG. 9 is a graph 900 of capsule velocities as a function of time when a polyp was detected.

In an exemplary embodiment of the disclosure, it was determined that the motion of a capsule in the gastrointestinal tract with polyps differs from the motion in the gastrointestinal tract without polyps. Optionally, a gastrointestinal tract that moves capsule 110 slower (e.g. due to the content typically consumed by the patient or physiological parameters) may tend to enable polyps to grow with a higher probability than a gastrointestinal tract that moves capsule 110 faster. Alternatively, the existence of polyps may be the sign of a weaker gastrointestinal tract and therefore moves slower. In graph 900, a large polyp was detected in the Cecum using a colonoscopy. As can be seen, there are differences in the pattern of the colon motility and capsule movements for a colon without polyps (graph 800) vs. a colon with a polyp (graph 900).

In an exemplary embodiment of the disclosure, an ensemble of clinical data from patients with known polyps (from colonoscopy investigation, CT imaging, capsule imaging or other modalities) and an ensemble of clinical data from patients without polyps (from colonoscopy investigation, CT imaging, capsule imaging or other modalities) are collected with motion recordings by recorder 120 to form a corpus of motion recordings with known polyp status. The corpus of motion recordings can be used to train a neural network classifier or other type of classifier. Accordingly. A pattern recognition algorithm using a trained neural network classifier (e.g. a convolutional neural network) or other such algorithm can be employed in program 115 to distinguish between a velocity pattern which correlates with the presence of polyps and a velocity pattern which correlates with the absence of polyps.

In some embodiments of the disclosure, program 115 may determine the approximate location of the polyp or which organ has a polyp (e.g. cecum, colon, small intestine or rectum) based on the motion pattern of capsule 110 as depicted e.g. in FIG. 9.

Alternatively or additionally, other classifying algorithms such as nearest K neighbors, Generative Adversarial Networks and others can be used to differentiate between patterns that indicate of the existence of polyps and patterns that indicate the absence of polyps. Likewise, other clinical data or combination of clinical data such as pressure, position based spectral analysis, angular changes over time and position of the capsule can be used alone or in combination with imaging data to provide an estimation regarding the presence or the absence of polyps in the tested patient.

Figure 10:
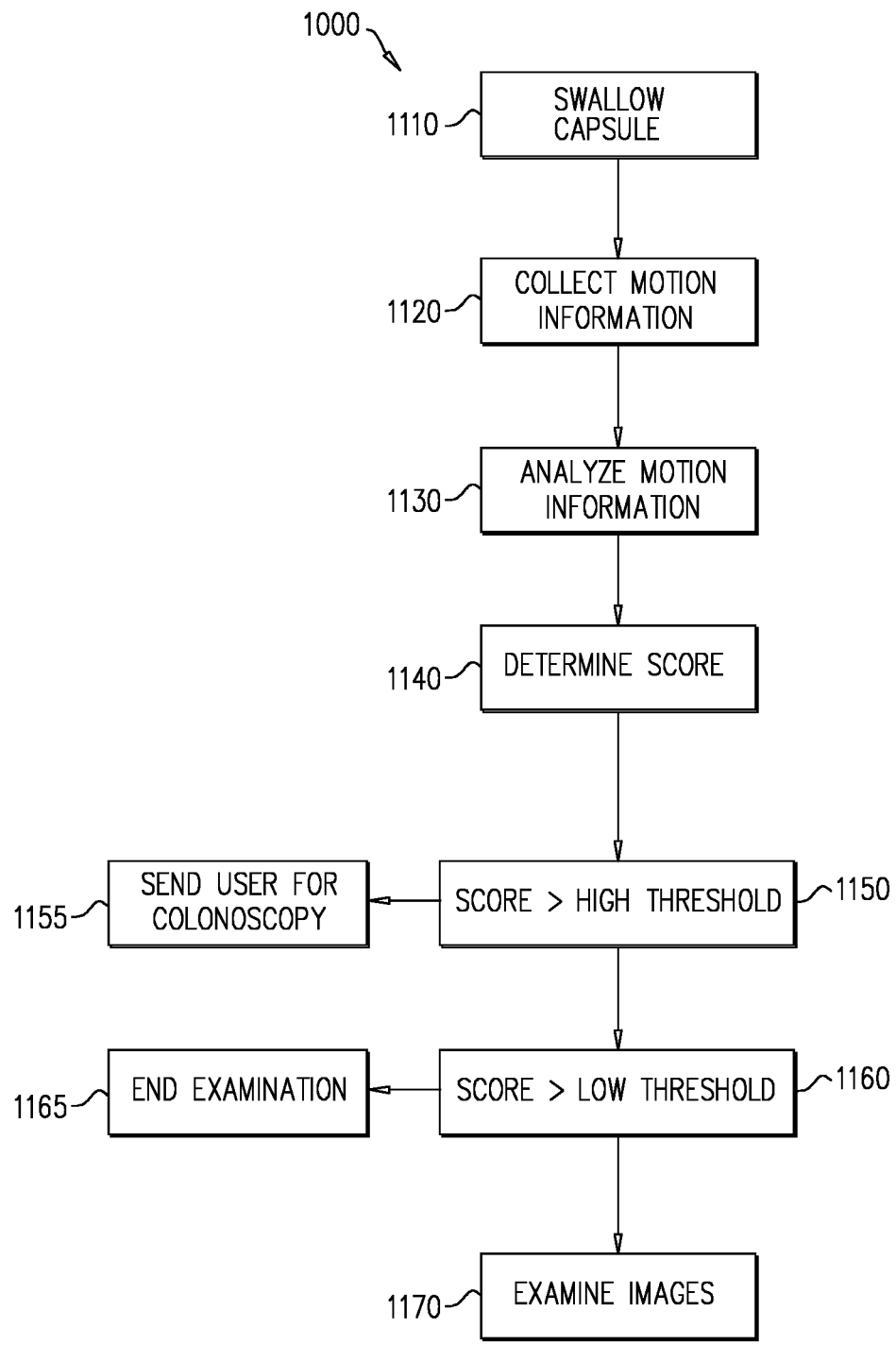
FIG. 10 is a flow diagram of a method of determining the existence of polyps based on capsule dynamics, according to an exemplary embodiment of the disclosure.

FIG. 10 is a flow diagram 1000 of a method of determining the existence of polyps based on capsule dynamics, according to an exemplary embodiment of the disclosure.

In an exemplary embodiment of the disclosure, the patient swallows (1110) capsule 110. Optionally, capsule 110 may include imaging capability, position tracking capability, pressure sensors and other sensors. Alternatively, capsule 110 may be a capsule without imaging capability. In an exemplary embodiment of the disclosure, capsule 110 with recorder 120 are capable of monitoring the position and motion of capsule 110 or at least capable of identifying when capsule 110 exits from the body of the patient. For example capsule 110 may provide a tracking signal to recorder 120 and when the signal becomes distant or disappears recorder 120 will conclude that the capsule 110 has exited from the body of the patient and can determine the time it took for the capsule 110 to traverse the patients gastrointestinal tract.

Accordingly, recorder 120 collects (1120) the capsule 110 motion information, which may include the position and velocity of the capsule throughout the gastrointestinal tract (e.g. as shown in FIGS. 8 and 9) or at least the time to traverse the gastrointestinal tract or specific organs.

In an exemplary embodiment of the disclosure, recorder 120 and/or computer 105 analyze (1130) the motion information and determine (1140) a probability score regarding the existence of polyps or abnormalities in the patient's gastrointestinal tract especially the colon 190. Optionally, the analysis (1130) may include use of a statistical model or neural networks to analyze motion patterns, or may simply include comparing the travel time of the capsule to a threshold value.

In an exemplary embodiment of the disclosure, if the probability score is greater than a high threshold value (1150), for example greater than 80%. Then it is assumed that the patient has polyps and should be sent (1155) to perform a colonoscopy to verify and treat the polyps. If however the probability score is less than the high threshold value and below a low threshold value (1160), for example below 20%. Then it is assumed that it is very unlikely that the patient has polyps (e.g. if the motion pattern (see FIGS. 8 and 9) indicates the absence of polyps). Optionally, recorder 120 and/or computer 105 provide a recommendation to end the examination (1165). If the probability score is between the low threshold value and the high threshold value (e.g. between 20-80%) then recorder 120 or computer 105 may suggest further tests (e.g. a colonoscopy or using a capsule with imaging capability) or may analyze images (1170) or other information if acquired by the capsule 110 to support or disprove the results.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

We claim:

1. A system for determining a probability of the existence of polyps in a gastrointestinal tract of a patient through capsule dynamics, comprising:
   a capsule that can be swallowed by a patient; wherein the capsule comprises a controller, a transceiver and one or more sensors that track information of position and/or motion of the capsule within the patient and transmit the information;
   a recorder comprising a transceiver and controller;
   wherein the recorder is worn by the patient and receives transmissions of the information from the capsule;
   wherein the system determines position or motion information of the capsule from the information received from the capsule, analyzes the position or motion information and determines a probability score representing the likelihood of the existence of polyps in the gastrointestinal tract of the patient; and wherein the system comprises a display that is provided with a message to notify the patient of further actions to be performed in response to the determined probability score; and wherein the information from the capsule is used to determine a time interval for traversing the gastrointestinal tract or specific organs within the gastrointestinal tract, and the probability score is based on the time interval.

2. The system according to claim 1, wherein the capsule includes an imaging system and the information provided by the capsule is used to reconstruct images of the gastrointestinal tract of the patient.

3. The system according to claim 2, wherein if the probability score is higher than a high threshold value the images are ignored and the patient is notified to perform a colonoscopy.

4. The system according to claim 2, wherein if the probability score is lower than a low threshold value the images are ignored and the patient is notified that further testing is not required.

5. The system according to claim 2, wherein if the probability score is lower than a high threshold value and higher than a low threshold value the images are analyzed to determine if to perform a colonoscopy.

6. The system according to claim 1, wherein the capsule uses the one or more sensors to determine a motion pattern of the capsule in the gastrointestinal tract of the patient and the system determines the probability score of the existence or absence of polyps based on the motion pattern.

7. The system according to claim 6, wherein the motion pattern is analyzed by a statistical model or a neural network classifier to determine the probability score.

8. The system according to claim 6, wherein a probable location of polyps or which organs within the gastrointestinal tract probably have polyps is determined based on the motion pattern.

9. A method of determining a probability of the existence of polyps in a gastrointestinal tract of a patient with a system including a capsule and a recorder based on capsule dynamics, comprising:

swallowing the capsule; wherein the capsule comprises a controller, a transceiver and one or more sensors that track information of position and/or motion of the capsule within the patient and transmit the information;

wearing the recorder, and receiving transmissions of information from the capsule by the recorder;

determining position or motion information of the capsule from the information received from the capsule;

analyzing the position or motion information to determine a probability score representing the likelihood of the existence of polyps in the gastrointestinal tract of the patient; and providing a message on a display to notify the patient of further actions to be performed responsive to the determined probability score; and wherein the information from the capsule is used to determine a time interval for traversing the gastrointestinal tract or specific organs within the gastrointestinal tract, and the probability score is based on the time interval.

10. The method according to claim 9, wherein the capsule includes an imaging system and the information provided by the capsule is used to reconstruct images of the gastrointestinal tract of the patient.

11. The method according to claim 10, wherein if the probability score is higher than a high threshold value the images are ignored and the patient is notified to perform a colonoscopy.

12. The method according to claim 10, wherein if the probability score is lower than a low threshold value the images are ignored and the patient is notified that further testing is not required.

13. The method according to claim 10, wherein if the probability score is lower than a high threshold value and higher than a low threshold value the images are analyzed to determine if to perform a colonoscopy.

14. The method according to claim 9, wherein the capsule uses the one or more sensors to determine a motion pattern of the capsule in the gastrointestinal tract of the patient and the system determines the probability score of the existence or absence of polyps based on the motion pattern.

15. The method according to claim 14, wherein the motion pattern is analyzed by a statistical model or a neural network classifier to determine the probability score.

16. The method according to claim 14, wherein a probable location of polyps or which organs within the gastrointestinal tract probably have polyps is determined based on the motion pattern.

* * * * *